(12) United States Patent
Yukino

(10) Patent No.: US 10,267,673 B2
(45) Date of Patent: Apr. 23, 2019

(54) INFORMATION PROCESSING DEVICE, INFORMATION PROCESSING METHOD, AND RECORDING MEDIUM

(71) Applicant: TANITA CORPORATION, Tokyo (JP)

(72) Inventor: Satsuki Yukino, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 0 days.

(21) Appl. No.: 15/905,930

(22) Filed: Feb. 27, 2018

(65) Prior Publication Data

US 2018/0283932 A1    Oct. 4, 2018

(30) Foreign Application Priority Data

Mar. 30, 2017  (JP) ................. 2017-067426

(51) Int. Cl.
| | |
|---|---|
| G08B 21/22 | (2006.01) |
| G01G 19/50 | (2006.01) |
| G08B 21/02 | (2006.01) |
| A61B 5/103 | (2006.01) |
| G01R 27/26 | (2006.01) |
| A61B 5/053 | (2006.01) |
| G01G 23/18 | (2006.01) |
| G16H 50/20 | (2018.01) |
| G16H 20/70 | (2018.01) |

(52) U.S. Cl.
CPC .......... *G01G 19/50* (2013.01); *A61B 5/0537* (2013.01); *A61B 5/1036* (2013.01); *G01G 23/18* (2013.01); *G01R 27/26* (2013.01); *G08B 21/02* (2013.01); *G16H 20/70* (2018.01); *G16H 50/20* (2018.01)

(58) Field of Classification Search
CPC ... A61B 5/0537; A61B 5/4869; A61B 5/0002; A61B 5/0538; A61B 5/4878; A61B 5/053; A61B 5/165; A61B 5/486; A61B 5/0484; A61B 5/16; G16H 10/20; G16H 50/30; G16H 15/00; G06F 19/3481; G06F 19/363

USPC ....... 340/573.1, 568.1, 568.8, 573.4, 636.15, 340/691.8, 3.1, 5.52, 5.82, 7.5, 7.55, 7.6, 340/10.1, 825.73

See application file for complete search history.

(56) References Cited

U.S. PATENT DOCUMENTS

| | | | | |
|---|---|---|---|---|
| 7,797,421 B1 * | 9/2010 | Scofield | ............... | G06F 15/173 709/203 |
| 2006/0258952 A1 * | 11/2006 | Stahmann | ............ | A61B 5/0537 600/547 |

(Continued)

FOREIGN PATENT DOCUMENTS

JP    2008-304421 A    12/2008

OTHER PUBLICATIONS

The extended European search report issued by the European Patent Office dated Aug. 21, 2018, which corresponds to EP18165000.3-1126 and is related to U.S. Appl. No. 15/905,930.

*Primary Examiner* — Daniel Previl
(74) *Attorney, Agent, or Firm* — Studebaker & Brackett PC

(57) ABSTRACT

A control unit of a body composition meter (an information processing device) obtains measurement information on a measurement habit when a user measures body information of himself/herself. The control unit determines a level of awareness of the user for health of himself/herself using the measurement information. The control unit notifies the user of information on health according to the level of health awareness.

10 Claims, 9 Drawing Sheets

(56) References Cited

U.S. PATENT DOCUMENTS

| | | | |
|---|---|---|---|
| 2008/0256445 A1* | 10/2008 | Olch | G06F 19/00 715/700 |
| 2010/0130831 A1* | 5/2010 | Sato | G01G 19/4146 600/300 |
| 2014/0032238 A1* | 1/2014 | Piao | G06Q 50/22 705/2 |
| 2014/0149139 A1* | 5/2014 | Bowen, Jr. | G06Q 50/24 705/3 |
| 2015/0289810 A1 | 10/2015 | Pacione et al. | |

* cited by examiner

FIG. 7

| | | REGULARITY OF MEASUREMENT TIMES | | |
|---|---|---|---|---|
| | | REGULATED | | NOT REGULATED |
| | | MEASUREMENT FREQUENCY/DAY | | |
| | | TWICE OR MORE A DAY | ONCE A DAY | |
| REGULARITY OF MEASUREMENT DATES | REGULATED | MEASUREMENT FREQUENCY/WEEK | SEVEN DAYS | A-1 | A-3 | B-1 |
| | | | SIX DAYS OR LESS | A-2 | A-4 | B-2 |
| | NOT REGULATED | | | C-1 | C-2 | D |

FIG. 8

| WEIGHT VARIATION VALUE | IMPEDANCE VARIATION VALUE | | |
|---|---|---|---|
| | LARGER THAN USUAL | | AS USUAL |
| | + | − | |
| LARGER THAN USUAL + | OVEREATING, DEHYDRATION, INSUFFICIENT SLEEP | OVEREATING, EDEMA, LACK OF EXERCISE | OVEREATING, INSUFFICIENT SLEEP, LACK OF EXERCISE |
| LARGER THAN USUAL − | DEHYDRATION, INSUFFICIENT SLEEP | EDEMA, INSUFFICIENT SLEEP, EXCESSIVE EXERCISE | TEMPERANCE IN EATING, INSUFFICIENT SLEEP |
| AS USUAL | DEHYDRATION | EDEMA, EXCESSIVE EXERCISE | APPROPRIATE EATING AND DRINKING |

FIG. 9

ADVICE

| LEVEL OF AWARENESS FOR HEALTH | EXAMPLE OF BASIC ADVICE (SEE FIG. 8) | EXAMPLE OF ADDITIONAL ADVICE | INFORMATION VOLUME | SPECIALIZATION OF INFORMATION |
|---|---|---|---|---|
| HIGH | Let's drink water well in the morning (as measures to dehydrate). | Review the amount of meal yesterday, let's make today the adjustment date. | MUCH | HIGH |
| HIGH | Let's reduce the amount of meal or increase the amount of exercise(as measures against overeating). | Even if there are such days occasionally there is no problem. It is important not to be too concerned about transient body composition change. | MUCH | HIGH |
| LOW | Keeping in mind to go to bed early is better (as measures against insufficient sleep) | Please leave interval between events of drinking party. | SMALL | LOW |

INFORMATION PROCESSING DEVICE, INFORMATION PROCESSING METHOD, AND RECORDING MEDIUM

TECHNICAL FIELD

The present invention relates to an information processing device, an information processing method, and a recording medium that notify information on health of a user himself/herself.

BACKGROUND ART

As an information processing device, there has been proposed a scale that obtains the number of days in which a weight variation of a user in a day is determined as within a reference width in a predetermined period and displays a proportion of the number of days to the predetermined period (see JP2008-304421A).

SUMMARY OF INVENTION

Even the user of the above-described scale changes a level of interest in health of himself/herself daily. However, even if the user changes the level of interest in health, since the above-described scale merely displays the proportion of the number of days in which the weight variation is small in the predetermined period, it is sometimes difficult for the user to maintain motivation to improve living activities.

An object of the present invention is to provide an information processing device, an information processing method, and a recording medium that achieve maintenance of and improvement in motivation of the user to improve living activities.

According to an aspect of the present invention, an information processing device includes a controller and a notifying unit. The controller is programmed to obtain measurement information on a measurement habit when a user measures body information of himself/herself, determine a level of awareness of the user for health of himself/herself on the basis of the measurement information obtained, and control the notifying unit so as to notify the user of information on health according to the level of awareness.

A non-transitory computer-readable recording medium including a program according to an aspect of the present invention, the program that causes a computer configured to process measurement information on a measurement habit when a user measures body information of himself/herself to execute: a determining step of determining a level of awareness of the user for health of himself/herself on the basis of the measurement information, and a notifying step of notifying the user of information on health according to the level of awareness.

An information processing method according to an aspect of the present invention includes: obtaining measurement information on a measurement habit when a user measures body information of himself/herself, a determining step of determining a level of awareness of the user for health of himself/herself on the basis of the measurement information; and a notifying step of notifying the user of information on health according to the level of awareness.

These aspects ensure notifying the user of the information on health meeting the level of awareness of the user through the determination of the level of awareness of the user for health of himself/herself. This ensures maintaining and improving motivation to improve living activities of the user.

BRIEF DESCRIPTION OF DRAWINGS

FIG. 7 is a drawing illustrating one example of a table used for determination of measurement frequency and regularity of the user of the one embodiment;

FIG. 8 is a drawing illustrating one example of a table used for determination of causes of variation of weight and impedance variations of the one embodiment; and FIG. 9 is a drawing illustrating one example of information on health displayed in a display unit in the body composition meter of the one embodiment.

DESCRIPTION OF EMBODIMENTS

The following describes an embodiment of the present invention with reference to the accompanying drawings and a similar material. This embodiment describes examples of applying an information processing device according to the present invention to a body composition meter that can measure body information such as a weight and a body fat.

Figure 1:
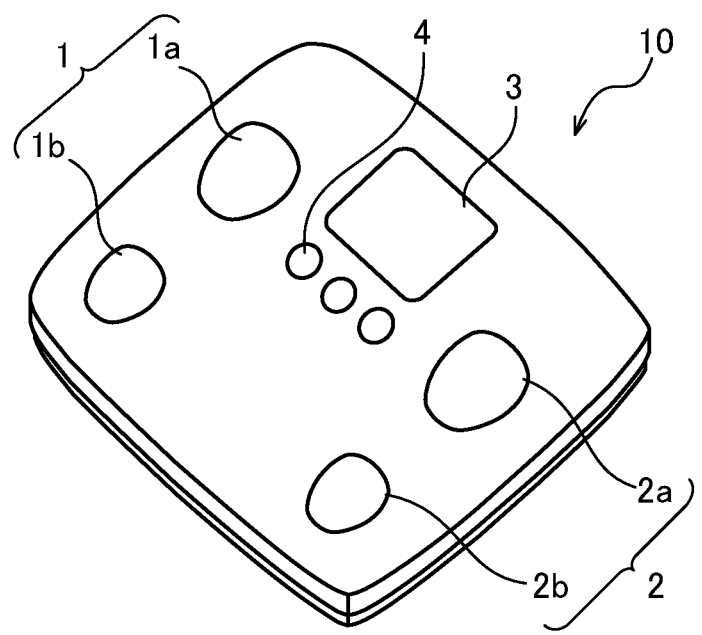
FIG. 1 is a drawing illustrating an appearance of a body composition meter to which an information processing device of one embodiment of the present invention is applied.

FIG. 1 is a drawing illustrating an appearance of a body composition meter 10 according to the embodiment. As illustrated in FIG. 1, the body composition meter 10 includes electrodes 1 and 2 to measure a biological impedance of a user, a display unit 3, and an operating unit 4. Although not appearing in the appearance illustrated in FIG. 1, the body composition meter 10 internally includes a load sensor 5 to measure the weight of the user and a timer 6 to obtain a time, a year, a month, and a day (see FIG. 2).

The electrodes 1 and 2 are constituted of energization electrodes 1a and 2a to flow a current to respective right and left feet of the user and measurement electrodes 1b and 2b to measure a voltage at both feet. The electrodes 1 and 2 are arranged separated from one another such that toes of both feet contact the energization electrodes 1a and 2a and heels of both feet contact the measurement electrodes 1b and 2b when the user steps on the body composition meter 10.

The display unit 3 functions as notifying means to notify the user of a measurement result or similar information. As the display unit 3, a liquid crystal display panel such as a Liquid Crystal Display (LCD) is employed. Details of contents of the displayed measurement result and similar information will be described later.

The operating unit 4 functions as an input interface that accepts an input operation by the user. Specifically, the operating unit 4 includes a plurality of operating buttons, which include, for example, an input button to input basic biological information such as a height, a sex, and an age and a power supply button to turn ON/OFF a power supply of the body composition meter 10. It should be noted that in the case where a touch panel functioning as the input interface is employed as the display unit 3, the operating unit 4 may be omitted and the display unit 3 may have the functions of the operating unit 4.

The load sensor 5 is, for example, a load cell, and measures a load applied from a top surface of the body composition meter 10 to measure the weight of the user. Not only merely measuring the weight of the user, the load sensor 5 can measure a change in the load when the user steps on the body composition meter 10.

The timer 6 obtains the current year, month, day, and time.

Figure 2:
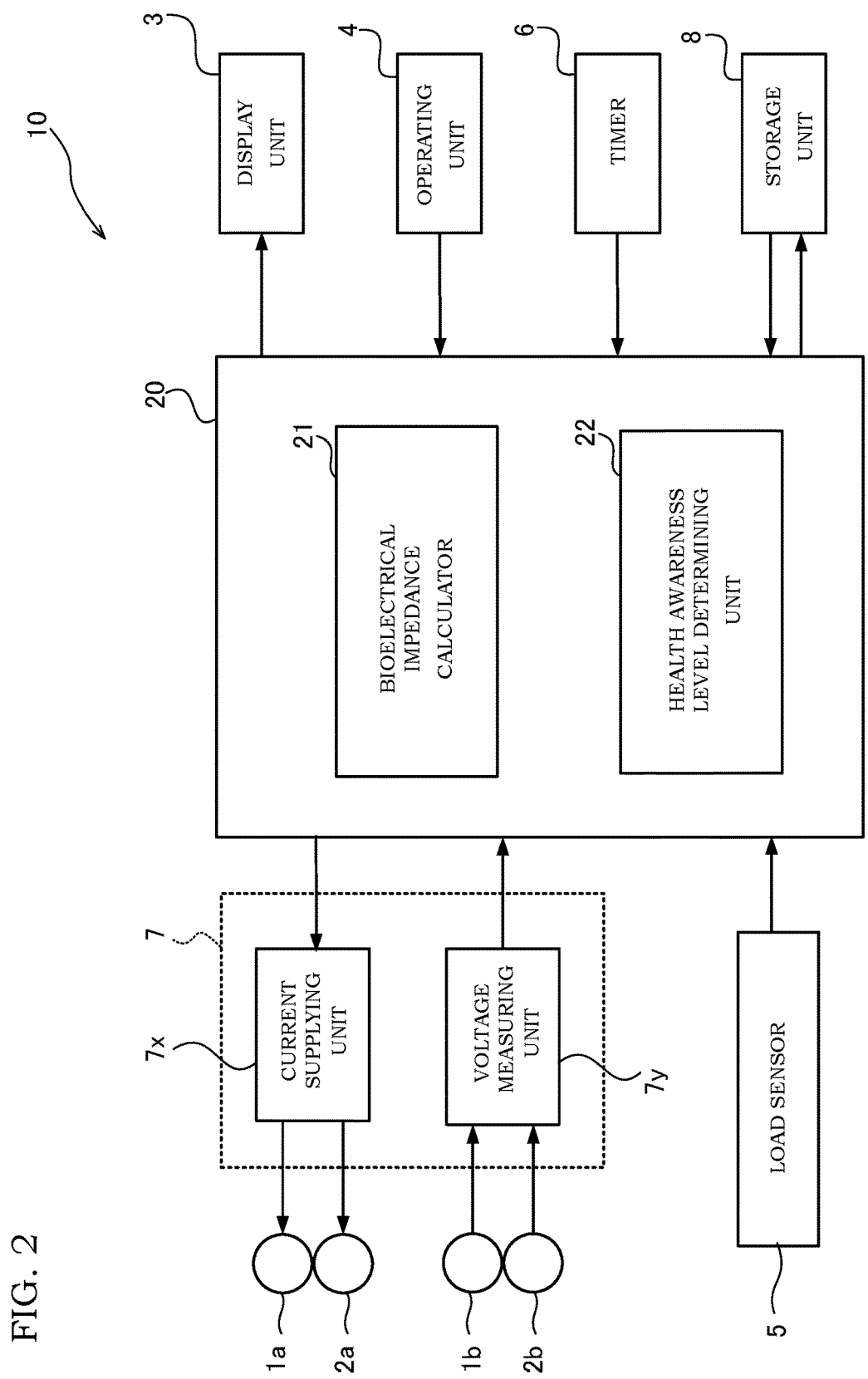
FIG. 2 is a block diagram illustrating one example of a function configuration included in the information processing device of the one embodiment.

FIG. 2 is a block diagram illustrating a main function configuration in the body composition meter 10 of the embodiment.

The body composition meter 10, in addition to the above-described display unit 3, operating unit 4, load sensor 5, and timer 6, mainly includes a biological impedance measuring unit 7, a storage unit 8, and a control unit 20, which includes a bioelectrical impedance calculator 21 and a health awareness level determining unit 22, as the function configuration.

The biological impedance measuring unit 7 includes a current supplying unit 7x coupled to the energization electrodes 1a and 2a and a voltage measuring unit 7y coupled to the measurement electrodes 1b and 2b. While the current supplying unit 7x supplies the user with an alternating current via the energization electrodes 1a and 2a, the voltage measuring unit 7y measures the voltage of the user via the measurement electrodes 1b and 2b.

The bioelectrical impedance calculator 21 calculates the biological impedance of the user on the basis of the respective values of the current supplied by the biological impedance measuring unit 7 and the measured voltage and stores the calculation result in the storage unit 8. It should be noted that it is only necessary to use a so-called Bioelectrical impedance analysis: a bioelectric impedance method (BIA) as a method of calculating the biological impedance, and the calculation may be similarly performed by the known body composition meter. While this embodiment describes the example of measuring the biological impedance between both feet, the measurement is not necessarily to be performed between both feet, and the biological impedance may be measured between both hands.

The storage unit 8 stores control programs that control behaviors of the body composition meter 10. That is, the storage unit 8 functions as a storage medium that stores the programs achieving the functions of the information processing device of this embodiment. The storage unit 8 includes a non-volatile memory (Read Only Memory: ROM), a volatile memory (Random Access Memory: RAM), and a similar memory.

The storage unit 8 associates the basic biological information input to the operating unit 4, biological impedance information from the biological impedance measuring unit 7, and information on the weight from the load sensor 5 with the time information from the timer 6 and stores the information.

The storage unit 8 further stores information on the body and health of the user, information conducible to promotion of health of the user, and character data, image data, and similar data used to display, for example, advice to improve disorder of life of the user in the display unit 3.

The control unit 20 includes a Central Processing Unit (CPU), input/output interfaces coupled to the above-described respective function configurations, and buses that couple these elements mutually. The control unit 20 reads the control program stored in the storage unit 8 and causes the central processing unit to execute the control program to control the respective units of the body composition meter 10 via the input/output interfaces.

More specifically, the control unit 20 controls the display unit 3, the operating unit 4, the load sensor 5, the timer 6, the biological impedance measuring unit 7, the storage unit 8, the bioelectrical impedance calculator 21, and the health awareness level determining unit 22 described later.

Here, the following describes a level of health awareness before describing the health awareness level determining unit 22.

The "level of health awareness" used in this embodiment is related to a concept of a behavior change stage model. The behavior change stage model is a model created on the basis of a way of thinking that, when a person changes actions, the person goes through five stages (a behavior change stage) starting from "a precontemplation stage," "a contemplation stage," "a preparation stage," "an action stage," and reaching "a maintenance stage." These respective stages differ in a degree of awareness (the level of awareness) for changing the self-action. In view of this, it is considered that, in the behavior change stage model, to advance the stage and change the actions of the person, it is necessary (effective) to grasp the current stage that the person is in and encourage the person according to each level of awareness.

That is, "the level of health awareness" is an application of the above-described behavior change stage to the action to improve the living regarding health and is defined as an index of how much the user is conscious about health of himself/herself. On the basis of the above-described way of thinking of the behavior change stage, determining and grasping the level of health awareness of the user ensures selecting further appropriate encouragement to improve the actions of the user.

On the basis of such way of thinking, the body composition meter 10 according to the embodiment includes the health awareness level determining unit 22, which determines high and low (the level of health awareness) of the awareness of the user for health of himself/herself, thus providing the information on health selected or created according to the determined level of health awareness to the user. More specifically, the body composition meter 10 according to the embodiment selects or creates the further appropriate advice conducible to improve the actions of the user meeting the level of health awareness of the user and provides the advice to the user. The following describes details of the configuration of the health awareness level determining unit 22.

Figure 3:
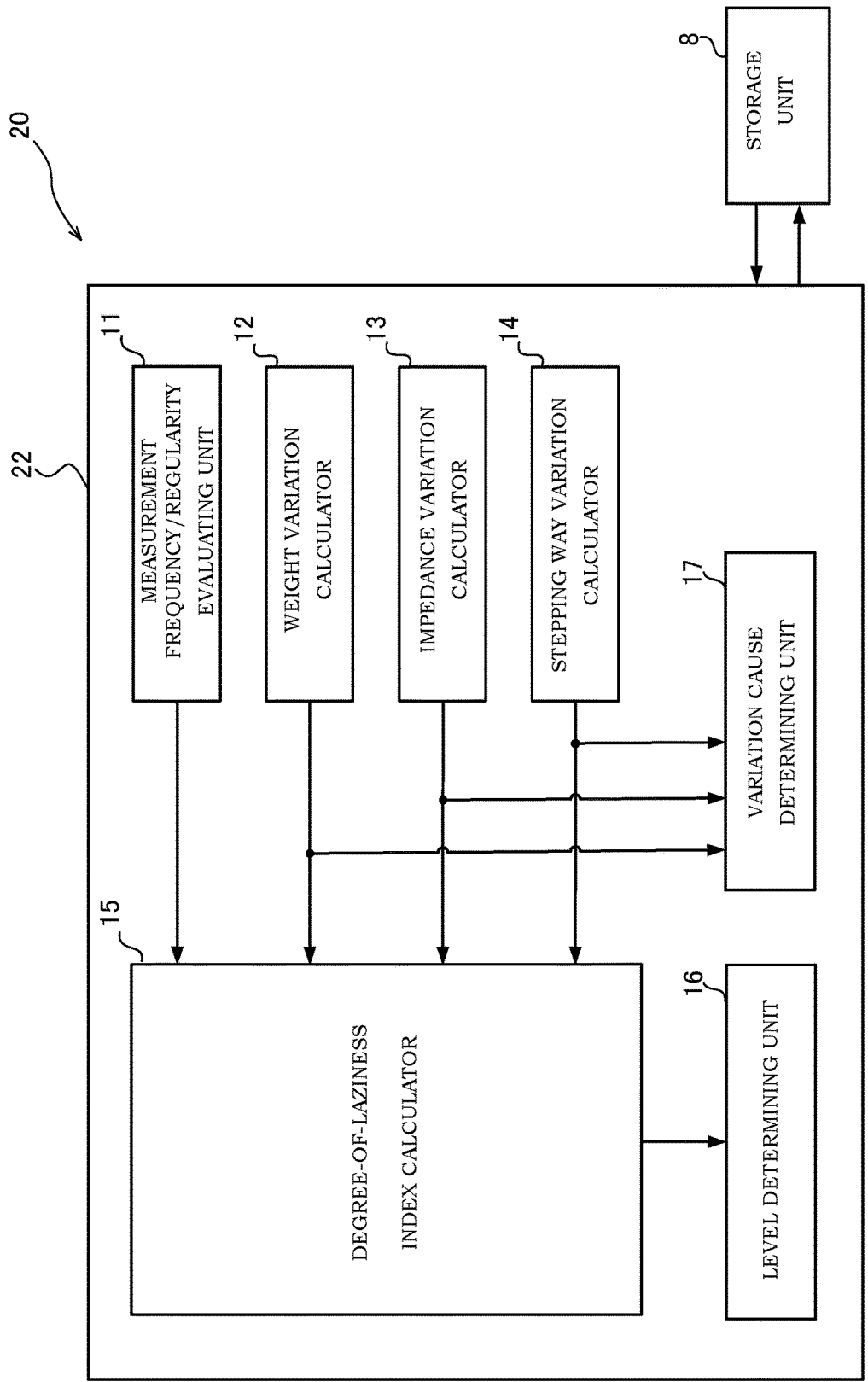
FIG. 3 is a drawing illustrating one example of a function configuration of a health awareness level determining unit included in the information processing device of the one embodiment.

FIG. 3 is a drawing illustrating the main function configuration of the health awareness level determining unit 22. The health awareness level determining unit 22 includes a measurement frequency/regularity evaluating unit 11, a weight variation calculator 12, an impedance variation calculator 13, a stepping way variation calculator 14, a degree-of-laziness index calculator 15, and a level determining unit 16. The health awareness level determining unit 22 further includes a variation cause determining unit 17 that determines causes of the variations on the basis of the calculation results from the respective weight variation calculator 12, impedance variation calculator 13, and stepping way variation calculator 14.

The measurement frequency/regularity evaluating unit 11 calculates the measurement frequency/regularity of the user (a pattern index) on the basis of the information on the year, month, day and time when the user uses the body composition meter 10, which is the information stored in the storage unit 8. Here, the measurement frequency is calculated from the number of usages in a predetermined period in units of days or in units of weeks. It should be noted that the predetermined period may be another period such as in units of months. The regularity is calculated from a measurement day or a measurement time when the measurement is performed several times. A habit (a measurement habit) regarding the measurement of the body information of himself/herself by the user can be grasped from the calculated measurement frequency/regularity of the user.

For example, when it is found from the grasped measurement habits that the user measures the body information of himself/herself more frequently and more regularly compared with previously, it can be estimated that the level of health awareness of this user is improved.

The weight variation calculator 12 calculates a variation value of a weight $x1$ of the user on the basis of at least two or more measured weight values stored in the storage unit 8. Here, the variation value $x1$ (the weight variation value $x1$) is one representing a degree of the weight variation of the user in numbers. For example, a variance value of the plurality of stored measured weight values is used.

The impedance variation calculator 13 calculates a variation value $x2$ of the impedance of the user on the basis of at least two or more measured biological impedance values stored in the storage unit 8. Here, the variation value $x2$ (the impedance variation value $x2$) is one representing a degree of the impedance variation of the user in numbers. Similar to the weight, a variance value of the plurality of measured biological impedance values stored in the storage unit 8 is used.

The stepping way variation calculator 14 calculates a variation value $x3$ of the way of stepping of the user on the body composition meter 10 on the basis of the measured data by the load sensor 5 stored in the storage unit 8. The following describes the calculation method for the variation value $x3$ (the stepping way variation value $x3$) with reference to FIG. 4.

Figure 4:
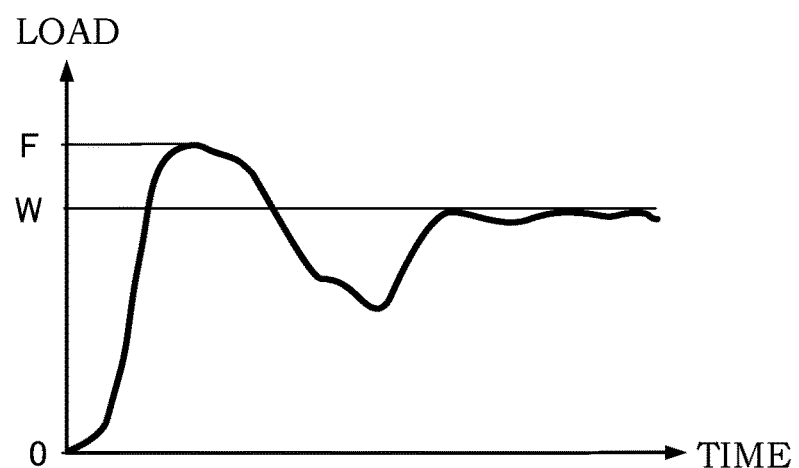
FIG. 4 is a drawing illustrating one example of a change in a load when a user steps on the body composition meter.

FIG. 4 is a drawing illustrating the change in the measured data (the stepping way index) from the load sensor 5 when the user steps on the body composition meter 10. In FIG. 4, the horizontal axis indicates the time while the vertical axis indicates the load. F in the drawing indicates the maximum value of the variation in load in a sequence of behaviors when the person steps on the body composition meter 10 and w indicates the measured weight value of the user.

As apparent from the drawing, when the weight of the person is measured, after the load steeply increases from the moment that the person steps on the body composition meter 10 and reaches the maximum value F, the value converges to the actual weight w while repeatedly decreasing and increasing. At this time, the gradient of increase in load, the maximum value F, the period until the converging, and a similar value vary depending on the way of stepping on the body composition meter 10. For example, when the user coarsely and swiftly steps on the body composition meter 10, the gradient of increase and the maximum value F become relatively large and the period until the value converges lengthens. Conversely, when the user calmly and slowly steps on the body composition meter 10, the gradient of increase and the maximum value F becomes relatively small and the period until the value converges becomes short.

Accordingly, the variation value $x3$ of the way of stepping of the user on the body composition meter 10 can be calculated through comparison between any one or more of the measured values of the magnitude of the gradient of the change in load, the difference between the actual weight w and the maximum value F, and the period until the value converges to the actual weight w with those identical kinds of the past measured values on the basis of the change in the measured data from the load sensor 5. For example, when the user disorders the life, since the user is likely to coarsely step on the body composition meter 10 more than usual, the stepping way variation value $x3$ becomes large. Accordingly, the use of the stepping way variation value $x3$ as the index to measure the level of health awareness allows determining the level of health awareness taking the degree of the disorder of life of the user into consideration.

The following continues the explanation returning to FIG. 3. The degree-of-laziness index calculator 15 calculates a degree-of-laziness index Z, which is represented in numbers as an index to measure the level of health awareness of the user on the basis of a trend specified from the various measured values (the measurement information) measured by the body composition meter 10. More specifically, the degree-of-laziness index calculator 15 calculates the degree-of-laziness index Z on the basis of the respective element indexes of the measurement frequency/regularity of the user, the variation value $x1$ of the weight, the variation value $x2$ of the impedance, and the variation value $x3$ of the way of stepping on the body composition meter 10. This embodiment determines that the larger the value of the degree-of-laziness index Z is, the lower the level of health awareness of the user is. A specific calculation method of the degree-of-laziness index Z will be described later.

The level determining unit 16 determines the level of health awareness of the user on the basis of the degree-of-laziness index Z calculated by the degree-of-laziness index calculator 15. The determination method is performed on the basis of the comparison between the degree-of-laziness index Z and a preset threshold. Note that, as this threshold, one value determinable by two levels, high and low may be set, and, for example, a plurality of values may be set so as to be determinable by equal to or more than five levels. The value of this threshold may be corrected according to a trend that the level of awareness of the user changes. That is, the threshold that the level determining unit 16 determines the level of health awareness of the user is appropriately settable. The determination result is output to the control unit 20 and stored in the storage unit 8.

The variation cause determining unit 17 determines the variation cause on the basis of at least one or more of the variation values of the weight variation value $x1$ calculated by the weight variation calculator 12, the impedance variation value $x2$ calculated by the impedance variation calculator 13, and the stepping way variation value $x3$ calculated by the stepping way variation calculator 14. For example, in the case where both the variation value $x1$ of the weight and the variation value $x2$ of the impedance are larger than the normal values, it can be estimated that the cause is overeating, dehydration, and insufficient sleep. This allows the body composition meter 10 to provide the user with the advice according to the level of health awareness of the user taking the cause estimated from the variation values such as the weight variation into consideration.

The respective configurations included in the body composition meter 10 are described above. The body composition meter 10 not only includes the above-described respective configurations and merely displays the measurement results regarding the body of the user by appropriately controlling these configurations in coordination but also can provide the user with the advice as the information on health selected or created according to the level of health awareness of the user.

Next, the following describes details of the control to provide the user with the advice according to the level of health awareness of the user by the body composition meter 10.

Figure 5:
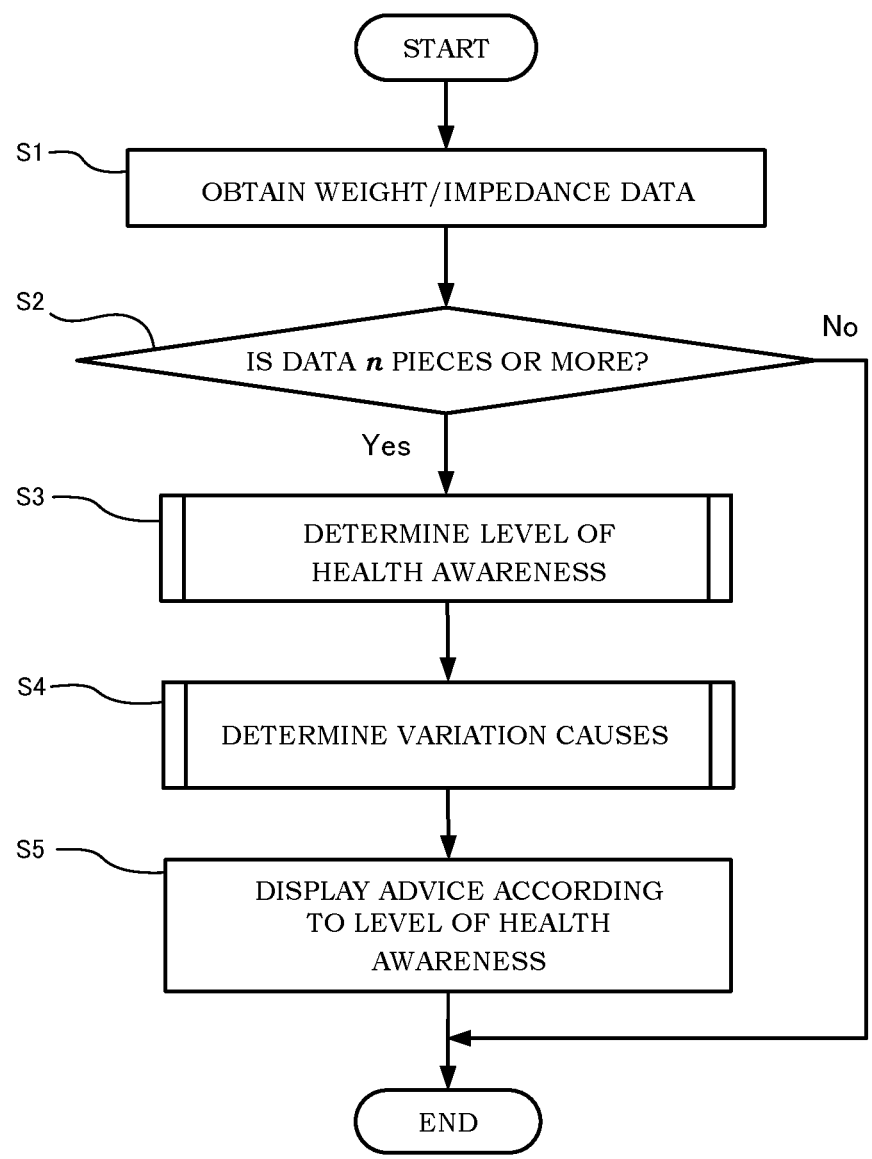
FIG. 5 is a flowchart illustrating a process procedure example regarding an information processing method of the one embodiment.

FIG. 5 is a flowchart illustrating a process procedure example of the control method of the body composition meter 10 of the embodiment.

At Step S1, the control unit 20 associates the measured weight value of the user obtained by the load sensor 5, the change data of the load when the weight is measured, and the measured impedance value of the user calculated by the bioelectrical impedance calculator 21 with the time information from the timer 6 and causes the storage unit 8 to store the associated data.

At Step S2, for determination whether the level of health awareness of the user can be calculated or not, the control unit 20 refers to the data stored in the storage unit 8 and determines whether the data (the measured values of the weight and the impedance of the user) obtained at Step S1 is stored by n pieces or more or not. While the n count in the embodiment is assumed as a value of at least two or more, the larger value is preferable for accurate determination of the level of health awareness. For example, with the n count of 30, the variation trend of, for example, the measurement habit and/or the weight of the user can be clear. Especially, assuming the measurement once a day, with the n count of 30 as the number of measurements in one month, the variation trend is further accurately seen.

The n compared at Step S2 may be set individually for each time slot. For example, some users usually perform the measurement twice a day, after wake-up in the morning and after bath at night. The weight of the person and the biological impedance change depending on the time slot. Accordingly, individually setting n for each time slot ensures the detection of the variation trend such as the measurement habit and/or the weight in each time slot, thereby ensuring further accurately grasping the level of health awareness of the user.

At Step S2, when the data obtained at Step S1 is n pieces or more, the subsequent process at Step S3 is executed to determine the level of health awareness on the basis of the obtained data of n pieces or more. When the data obtained at Step S1 is less than n pieces, it is determined that the measurement frequency and regularity of the user cannot be accurately calculated and the process regarding the determination of the level of health awareness shown in this flowchart is terminated.

At Step S3, the control unit 20 controls the health awareness level determining unit 22 to determine the level of health awareness of the user. The following describes the process procedure of the control regarding the determination of the level of health awareness with reference to FIG. 6.

Figure 6:
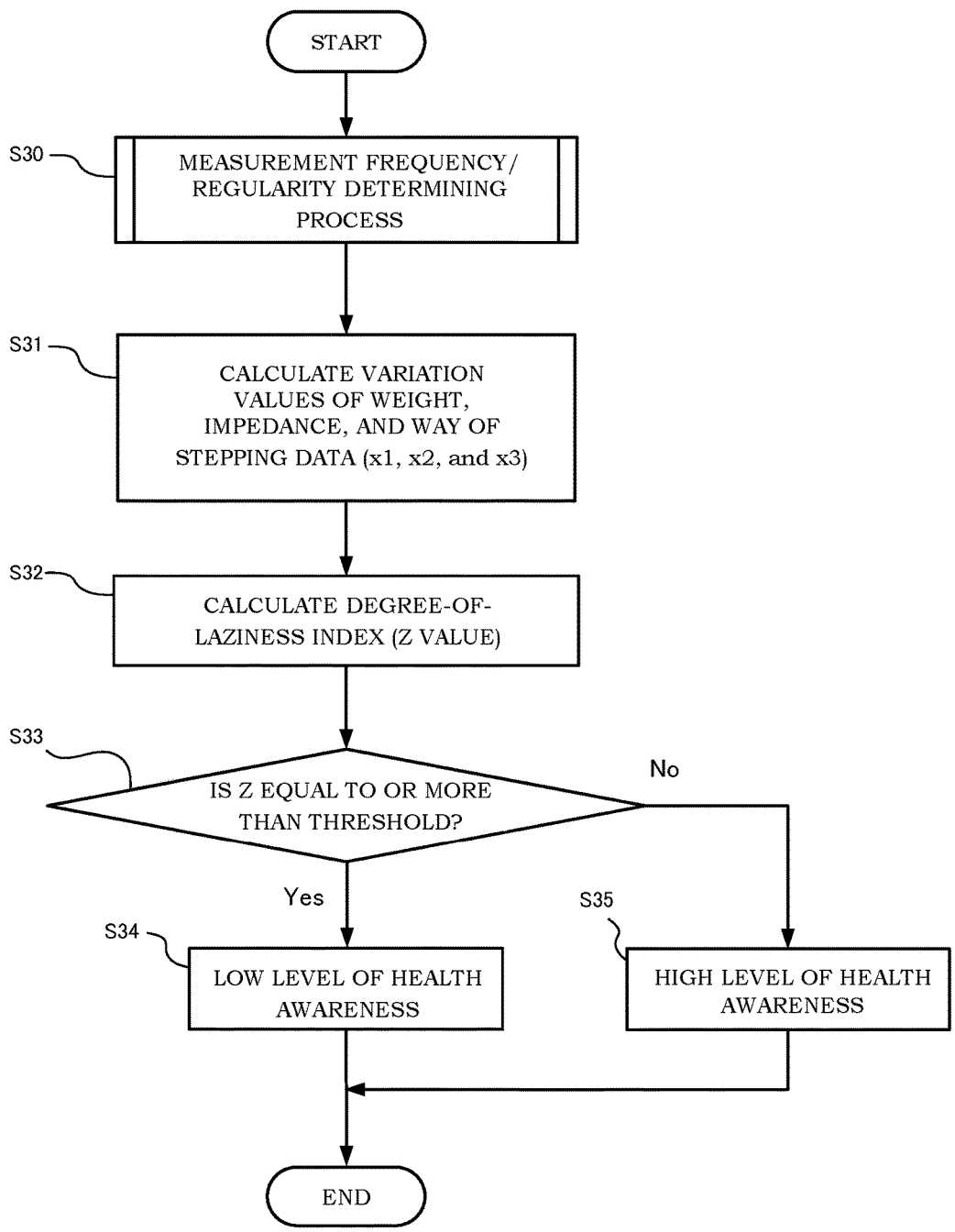
FIG. 6 is a flowchart illustrating a process procedure example regarding health awareness level determination of the one embodiment.

FIG. 6 is a flowchart illustrating a process procedure example of a process (a health awareness level determining process) to determine the level of health awareness of the user executed by the health awareness level determining unit 22 of the embodiment.

At Step S30, the health awareness level determining unit 22 determines the measurement frequency and regularity of the user. More specifically, for the calculation of the degree-of-laziness index Z described later, the health awareness level determining unit 22 refers to a table illustrated in FIG. 7 from the time information associated with the measured data of the user stored in the storage unit 8 to represent the measurement frequency and regularity of the user in numbers for evaluation.

The measurement frequency and regularity of the user represented in numbers are used for the calculation of the degree-of-laziness index Z as a measurement frequency/regularity determination value b (hereinafter referred to as a measurement habit determination value b). It should be noted that the smaller the measurement habit determination value b is, the smaller the degree-of-laziness index Z is, and the level of health awareness is determined as high.

FIG. 7 is a drawing illustrating one example of the table (hereinafter referred to as a measurement habit table) for the determination of the measurement frequency and regularity of the user. In the measurement habit table, the regularity of the measurement dates obtainable from the measured data of the user is made to correspond to the regularity of the measurement times mutually. Respective cells from A-1 to D illustrated in the table are related to the magnitude of the measurement habit determination value b. That is, the value of the measurement habit determination value b is set such that A-1 is the smallest, gradually becomes large from A-2 to A-4, B-1, and C-2, and D is the largest value (A-1<A-2<A-3<A-4<B-1<B-2<C-1<C-2<D).

In the measurement habit table illustrated in FIG. 7, the regularity of the measurement dates is classified into "Regulated" and "Not regulated." Compared with the case where the measurement dates are not regulated, the case where the measurement dates are regulated is set so as to have the smaller measurement habit determination value b. For example, even the measurement once a week, in the case where the measurement dates are every Monday, it is determined that the measurement dates are regulated. Even when the measurement dates are regulated, the measurement is classified into the measurements every day, seven days a week; and the measurements at six days or less in a week from the aspect of the measurement frequency. The smaller measurement habit determination value b is set as the measurement frequency (the measurement at seven days a week) becomes high.

The regularity of the measurement times is also classified into "Regulated" and "Not regulated," compared with the case where the measurement times are not regulated, the case where the measurement times are regulated is set so as to have the small measurement habit determination value b. Even when the measurement times are regulated, the measurement is classified into the measurements twice or more a day and the measurements only once a day from the aspect of the measurement frequency. The smaller measurement habit determination value b is set as the measurement frequency (the measurement twice or more a day) becomes high.

That is, with the measurement habit table of this embodiment, both the regularity of the measurement dates and the regularity of the measurement times are made to correspond to one another for evaluation. This allows the determination by representing the degrees of the measurement frequency and regularity of the user contributing to the level of health awareness in numbers. It should be noted that, in the measurement habit table of this embodiment, the case where the measurement dates are regulated is set to have the smaller measurement habit determination value b compared with the case where the measurement times are regulated. This is because it can be estimated that the longer the user maintains a concern to health of himself/herself, the higher the level of health awareness of the user is, from the aspect of persistence of awareness. Here, compared with the regularity of the measurement times, the regularity of the measurement dates reflects the regularity of long-term measurement.

It should be noted that the respective values of the number of times and the number of days shown in the measurement habit table illustrated in FIG. 7 are examples and therefore may be appropriately changed.

At Step S31 in FIG. 6, the health awareness level determining unit 22 calculates the weight variation value x1, the impedance variation value x2, and the stepping way variation value x3, which are found by representing the variations of the respective element indexes regarding the weight, the impedance, and the way of stepping in numbers. As the respective variation values of the embodiment, while the variance values of the respective element indexes may be used as described above, the values always need not to be the variance values. For example, the values may be differences between the maximum values and the minimum values of the respective element indexes. It is only necessary that the values are values (variation indexes) proportionate to the amounts of variation of the respective measured values.

The variation values of the respective element indexes are more preferably calculated by the measurement time slots. As described above, the weight of the person and the biological impedance change depending on the time slot. For example, it is known that the weight of the person is usually heavier by several hundred grams at night compared with the weight in the morning caused by a balance between metabolism and eating and a similar factor. Meanwhile, it is known that the biological impedance of the person becomes higher at wake-up compared with the biological impedance before going to bed. It is also considered that the trend of the way of stepping on the body composition meter 10 slightly changes between immediately after the wake-up and immediately before going to bed. Accordingly, when the variation values of the respective element indexes are calculated by the measurement time slots as described above, deviations of the respective element indexes caused by the different measurement time slots can be eliminated, thereby ensuring further accurately determining the level of health awareness of the user.

For example, with the measurements by 30 times, in the case where the measurement time slots are largely biased, such as the measurements by three times in the morning and the measurements by 27 times at night, the measurement time slot at which the measurements are performed many times may be specified, and the variation values of the respective element indexes may be calculated only from the measured values in the specified measurement time slot.

Thus, when the variation values (x1, x2, and x3) of the respective element indexes are calculated at Step S31, the health awareness level determining unit 22 executes a process at Step S32 to calculate the degree-of-laziness index Z on the basis of the variation values of the respective element indexes.

At Step S32, the health awareness level determining unit 22 calculates the degree-of-laziness index Z. The degree-of-laziness index Z is a value representing a degree of laziness and a degree of indifference of the user to the action to improve the living to promote health of himself/herself in numbers as an index to measure the level of health awareness. The degree-of-laziness index Z is calculated on the basis of the above-described measurement habit determination value b and the variation values x1, x2, and x3 of the respective element indexes. The degree-of-laziness index Z is, for example, calculated using the following Formula (1).

[Formula 1]

$$Z = \frac{a1x1 + a2x2 + a3x3}{3} + b \tag{1}$$

Note that Z in Formula (1) is the degree-of-laziness index, x1 is the weight variation value, x2 is the impedance variation value, x3 is the stepping way variation value, b is the measurement habit determination value, and a1, a2, and a3 are coefficients to weight the respective element indexes. The value "3" dividing (a1x1+a2x2+a3x3) is the number of the element indexes.

The coefficients a1, a2, and a3 of the embodiment may be individually set taking the levels of contribution of the above-described respective element indexes to the level of health awareness into consideration. Alternatively, in addition to the consideration of the level of contribution or instead of the level of contribution, the coefficients a1, a2, and a3 may be set taking the measurement frequency/regularity into consideration.

In the case where the coefficients a1, a2, and a3 are set taking the levels of contribution of the respective element indexes to the level of health awareness into consideration, for example, coefficients with which a relative difference in magnitude between average values of the respective element indexes is compensated are set such that the values of the three element indexes can be uniformly treated as long as the levels of contribution of the respective element indexes to the level of health awareness are identical. To increase or reduce the level of contribution of a specific element index to the level of health awareness, it is only necessary to appropriately adjust the magnitude of the value of the coefficient of the target element index after the compensation of the relative difference in magnitude of the average values.

In the case where the coefficients a1, a2, and a3 are set taking the measurement frequency/regularity of the respective element indexes into consideration, similar to the measurement habit determination value b, the values of the respective coefficients a1, a2, and a3 may be set with reference to the table illustrated in FIG. 7. Note that the body composition meter 10 of this embodiment measures the respective element indexes at the identical timing; therefore, the difference in magnitude on the basis of the measurement frequency/regularity does not occur in the respective coefficients a1, a2, and a3 in principle. Meanwhile, by the respective coefficients thus set, the measurement frequency/regularity of the user substantially act on the magnitude of the degree-of-laziness index Z. Accordingly, the level of health awareness of the user can be determined with putting further importance on the measurement frequency/regularity of the user.

At Step S33, the health awareness level determining unit 22 determines whether the degree-of-laziness index Z is equal to or more than a predetermined threshold or not to determine the level of health awareness of the user. Since this embodiment determines the level of health awareness of the user by the two levels, high and low, this threshold is a predetermined one value. The threshold in this case is appropriately set on the basis of, for example, a value taking an average value of general adult into consideration or an average value in a predetermined period from the past data of the user.

It should be noted that this threshold may be changed appropriately according to the calculation method of the degree-of-laziness index Z. For example, the degree-of-laziness index Z is calculated without dividing ($a_1x_1+a_2x_2+a_3x_3$) by the number of element indexes (3) as shown in Formula (1), and, instead of this, this threshold may be changed to a value found by multiplying this threshold by the number of element indexes (3).

Instead of Formula (1), for example, the degree-of-laziness index Z may be calculated using the following Formula (2).

[Formula 2]

$$Z = \frac{x1}{c1} + \frac{x2}{c2} + \frac{x3}{c3} + b \quad (2)$$

Note that c1, c2, and c3 are population parameters to weight the respective element indexes.

With Formula (2), changing the values of the population parameters c1, c2, and c3 of the respective element indexes instead of the coefficients a1, a2, and a3 shown in Formula (1) ensures adjusting the levels of contribution of the respective element indexes to the level of health awareness. For example, it is only necessary to reduce the value of c2 to increase the level of contribution of the impedance variation value x2 to the level of health awareness.

At Step S33, when the degree-of-laziness index Z is equal to or more than the threshold, the health awareness level determining unit 22 determines that the level of health awareness of the user is low (Step S34) and terminates the health awareness level determining process.

Meanwhile, when the degree-of-laziness index Z is smaller than the threshold, the health awareness level determining unit 22 determines that the level of health awareness of the user is high (Step S35) and terminates the health awareness level determining process.

The details of the health awareness level determining process executed at Step S3 in the flowchart illustrated in FIG. 5 are described above. The following continues the explanation returning to FIG. 5.

At Step S4, the variation cause determining unit 17 determines the causes of the variation of the respective element indexes (the variation causes) on the basis of the variation values (x1, x2, and x3) calculated in the health awareness level determining process. The variation cause is specified by estimating at least one of the living (the action) and a body condition of the user. The variation cause may be specified from the one element index or may be specified from the plurality of element indexes. For example, in the case where the weight variation as the one element index is large, the overeating, the insufficient sleep, or a similar factor is a possible cause. The determination making the weight variation to correspond to the impedance variation allows further detailed determination of the variation cause (see FIG. 8).

FIG. 8 is a drawing illustrating one example of a determination table (a variation cause determination table) used to determine the variation causes of the weight and the impedance variations. The variation cause determining unit 17 refers to the variation cause determination table illustrated in FIG. 8 to determine the variation causes of the weight and the impedance.

In the variation cause determination table illustrated in FIG. 8, the weight variation and the impedance variation are both classified into two categories, whether the respective amounts of variation are larger than usual or are as usual. The case of the amount of variation larger than usual is additionally classified into two categories, whether the variation varies on a negative side or a positive side with respect to the usual. That is, in the variation cause determination table illustrated in FIG. 8, since the weight variation and the impedance variation are made to correspond to one another each classified into the three patterns, the variation cause can be determined from the categories of nine patterns.

It should be noted that the value of "Usual" as the reference for the determination of the magnitude of the amount of variation may be preset from, for example, the average value of the general adult males taking the height, the sex, and a similar factor of the user into consideration or may be set from the average value of the past measured values in the predetermined period measured by the user in the past.

With the variation cause determination table illustrated in FIG. 8, when both the weight variation and the impedance variation largely vary to the positive side, it can be determined that the variation cause is dehydration, the overeating, and/or the insufficient sleep. With such determination made, it is estimated that an event that harms health has occurred in the living of the user from the variation cause. For example, with the variation cause of the dehydration, the overeating, and/or the insufficient sleep, it can be estimated that an event leading to alcohol ingestion, the overeating, and/or the insufficient sleep, such as a drinking party has taken place on the previous day.

If the alcohol ingestion, the overeating, and/or the insufficient sleep continues, for example, a mental condition of the user such as a trend of the user being stressful can be estimated, not only the event.

The storage unit 8 once stores the information on the variation causes thus determined, the event estimated from the variation causes, and similar information together with the determination result of the level of health awareness, and the information is reflected to the contents of the advice displayed in the display unit 3 at Step S5.

At Step S5, the control unit 20 displays the advice according to the level of health awareness of the user determined at Step S3 in the display unit 3. FIG. 9 shows an example of the advice displayed according to the level of health awareness of the user.

FIG. 9 is a drawing illustrating one example of the advice presented to the user according to the level of health awareness. As illustrated in the drawing, the advice presented to the user with this embodiment includes basic advice independent of the level of health awareness and additional advice added according to the level of health awareness of the user.

The above-described additional advice changes the information volume and the contents according to the level of health awareness. Specifically, the higher the level of health awareness is, the larger the information volume is and the contents are further highly specialized. Meanwhile, the lower the level of health awareness is, the smaller the information volume is and the specialization of the contents becomes low. It should be noted that while the contents of the information become further specific as the specialization becomes high, the contents of the information become further general as the specialization lowers.

By thus setting the advice presented to the user, the advice of higher specialization can be provided more as the level of health awareness becomes high. Accordingly, the user who has the high level of health awareness and desires to have more effective guideline or knowledge to improve health of himself/herself is likely to maintain and improve motivation to improve the living of himself/herself. Meanwhile, providing much information with high specialization to the person with low level of health awareness possibly results in a drop in motivation for improvement in living of himself/herself due to, for example, the user feeling a burden. Therefore, reducing providing much information with high specialization to the person with the low level of health awareness ensures eliminating a situation of drop in motivation of the user for the improvement in living.

Thus, changing the advice according to the level of health awareness allows providing the advice meeting the level of health awareness of the user to the user. Accordingly, the user can further effectively maintain and improve the motivation to promote health of the user or improve the disorder of life.

The following describes actions and effects of this embodiment.

With this embodiment, the control unit 20 provided with the body composition meter 10 (the information processing device) obtains the measurement information on the measurement habit when the user measures the body information of himself/herself from the load sensor 5, the timer 6, and the biological impedance measuring unit 7. The control unit 20 determines the level of awareness (the level of health awareness) of the user for health of himself/herself on the basis of the measurement information and notifies the user of the information on health according to the level of health awareness via the display unit 3.

Thus, the body composition meter 10 of this embodiment can provide the information on health according to the level of health awareness of the user to the user, ensuring effectively maintaining and improving the motivation to improve the living activities of the user.

With this embodiment, the measurement information obtained by the control unit 20 includes the pattern index indicative of at least any one of the measurement frequency and regularity when the user measures the measurement information of himself/herself. This allows the health awareness level determining unit 22 to take the measurement frequency or regularity indicative of the measurement habit of the user into consideration when the health awareness level determining unit 22 determines the level of health awareness of the user.

With this embodiment, the measurement information obtained by the obtaining unit includes the variation indexes. The variation indexes are the indexes indicative of the amounts of variation of the body information calculated on the basis of the plurality of measured values through the measurements of the body information of himself/herself by the user in time series. This allows the health awareness level determining unit 22 to take the actual change situation in the body of the user or the actions of the user in the predetermined period into consideration when the health awareness level determining unit 22 determines the level of health awareness of the user.

It should be noted that since the body information includes at least any one of the weight and the biological impedance of the user, the health awareness level determining unit 22 can determine the level of health awareness of the user taking at least any one of the amounts of variation of the weight and the impedance of the user (the weight variation value x1 and the impedance variation value x2) into consideration.

The measurement information includes the stepping way index indicative of the change in load when the user measures the weight of himself/herself. This allows the health awareness level determining unit 22 to determine the level of health awareness of the user taking the change in action when the user steps on the body composition meter 10 and measures the body information of himself/herself (the stepping way variation value x3) into consideration.

This embodiment includes the degree-of-laziness index calculator 15 constituting degree-of-laziness index calculating means, which calculates the degree-of-laziness index Z as the index to measure the level of health awareness of the user on the basis of the trend specified from the measurement information, that is, the trend of the result of the measurement (measurement result trend). The health awareness level determining unit 22 determines the level of health awareness of the user on the basis of the degree-of-laziness index Z.

This ensures representing the trend of the measurement results derived from the measurement information related to the body and the action of the user in numbers, thereby ensuring further quantitatively evaluating the level of health awareness. Additionally, since the respective pieces of measurement information can be collectively represented in numbers as the degree-of-laziness index Z, which is the index to measure the level of health awareness, the increase and decrease of the number of element indexes to measure the level of health awareness can be easily treated.

The degree-of-laziness index calculator 15 weights the measurement information according to the level of contribution to the level of health awareness. This ensures further accurately determining the level of health awareness of the user compared with the case of using the variation values calculated from the respective pieces of measurement information as it is.

This embodiment includes the control unit 20, which changes the information on health displayed in the display unit 3 according to the level of health awareness determined by the health awareness level determining unit 22. Since this allows providing the advice on health or similar information meeting the level of health awareness of the user to the user, the user can effectively maintain and improve the motivation to improve the living activities of the user.

This embodiment includes the variation cause determining unit 17 constituting variation cause determining means to determine the variation cause of the measurement information. The display unit 3 provides the advice regarding health according to the variation cause determined by the variation cause determining unit 17 to the user. This ensures providing the further specific advice regarding health meeting the level of health awareness of the user to the user, thereby allowing the user to further effectively maintain and improve the motivation to improve the living activities.

While the embodiment of the present invention is described above, the above-described embodiment describes merely a part of application examples of the present invention and the gist does not limit the technical scope of the present invention to the specific configuration of the embodiment. The present invention, for example, includes the following modifications.

<Modifications>

For example, while the description that the above-described level of health awareness is determined from the degree-of-laziness index Z calculated from the measurement frequency and regularity when the user measures the body information of himself/herself and the variation values of the weight, the impedance, and the way of stepping is given above, the embodiment is not necessarily limited to this. For example, the level of health awareness according to the present invention may be determined from only any one of the measurement frequency and regularity of the user. In this case, for example, the measurement frequency of the user may be classified into two levels, three times or more in a week and less than three times, and it may be determined that the measurement frequency of three times or more in a week as the high level of health awareness and less than three times in a week as the low level of health awareness.

The element indexes used to calculate the above-described degree-of-laziness index Z need not to be limited to three, the weight, the impedance, and the way of stepping, and it is only necessary that the element index is at least one or more and another element index may be added or substituted.

As other element indexes, for example, a heartbeat, an amount of activity, sleeping (hours of sleep, a bedtime, an hour of rising, and a quality of sleep), reactivity to the switch, and the way of handling the body composition meter 10 of the user may be used. It is only necessary to measure these element indexes by the known method. With the use of another known measurement device, the body composition meter 10 can obtain the measured data by this measurement device through communications or a similar method to calculate the variation values of the respective element indexes.

The reactivity to the switch can be calculated from, for example, a period (a reaction period) from when the display unit 3 displays a command to press the switch and until the user presses the switch on the operating unit 4 in response to this command. With the body composition meter 10 further including an acceleration sensor, the way of handling the body composition meter 10 can be quantitatively measured from, for example, a vibration and a movement speed when the body composition meter 10 is moved to a predetermined position to measure the weight.

Not only used to calculate the variation value (the stepping way variation value x3) measurable from the load change data illustrated in FIG. 4, the load sensor 5 described in the above-described embodiment can also be configured to obtain a barycentric position (a load balance) or a body sway as information on which foot is placed first among the right and left feet (a dominant leg) and the posture (the standing position posture) as the element indexes.

To obtain such element indexes, for example, the load sensors 5 may be disposed by two in total at the right and left of the rectangular body composition meter 10 or by four in total near the four corners. The measurements of the load by the respective load sensors 5 thus configured ensures the measures of the dominant leg when the user steps on the body composition meter 10, the barycentric position of the user, and the body sway.

It should be noted that, to calculate the degree-of-laziness index Z using the four or more element indexes, it is only necessary to use the following Formula (3) instead of Formula (1).

[Formula 3]

$$Z = \frac{a1x1 + a2x2 + a3x3 + \ldots + anxn}{n} + b \quad (3)$$

The n shown in Formula (3) is defined as the number of element indexes.

The threshold used to determine the level of health awareness in the above-described embodiment can also be set, for example, as follows. That is, not only for the determination of the level of health awareness in phases on the basis of the degree-of-laziness index Z, this threshold may be set for each element index to allow the determination with the thresholds classified into a large number of types. The thresholds thus set allow the level of health awareness of the user to be classified into various types in combination with the determination results of the respective element indexes.

For example, the combinations of nine patterns of classification by the measurement habit determination value b according to the measurement frequency and regularity in stages, two patterns of classification by the presence/absence of the weight variation, two patterns of classification by the presence/absence of the impedance variation, and two patterns of classification by the presence/absence of the way of stepping variation allow the determination classifying the level of health awareness of the user into 72 patterns.

The level of health awareness of the user may be further classified into various types by the combination of the determination results such as a figure and a body balance of the user determined by another known method.

A life rhythm and a degree of the disorder of life of the user can be estimated from a change trend of the measurement frequency and regularity, the weight as the element index, the variation trend of the impedance, a habit of the way of stepping of the user, and a similar factor together with the level of health awareness of the user. Accordingly, the advice taking the life rhythm and the degree of the disorder of life of the user into consideration may be provided to the user together with the level of health awareness.

The information on health of the user displayed in the display unit 3 is not limited to the advice shown in FIG. 9. For example, only the determination result of the level of health awareness or only the point related to the degree-of-laziness index Z may be displayed. The display format, not only merely displays the values or the characters, but may also perform the display in the format of a bar graph and drawings and/or such that characters such as animals change according to the level of health awareness.

The display may be devised so as not to bore the user whose usage frequency is high, especially the user who performs the measurement every day, by, for example, changing the displayed advice or drawing or a similar display every day. For example, rare word and character or a similar figure, appearing only at a certain specific timing may be set to be displayed, for example only when the level of health awareness is determined to be improved and only when the measurements are performed for successive 300 days. Thus, changing the display contents in the display unit 3 in conjunction with the measurement habit and/or health improvement situation conducible to the level of health awareness of the user allows adding a game element to the daily measurements. Accordingly, the motivation for health improvement of himself/herself can be further maintained and improved without boring the user.

The display unit 3 is not necessarily to always have a configuration integrally provided with the body composition meter 10 but is substituted by a screen in a communication terminal such as a smart phone owned by the user. In this case, it is only necessary that this communication terminal receives data regarding the level of health awareness determined by the body composition meter 10, the advice according to the level of health awareness, or similar data through communications and displays the data in this screen. This communication terminal may obtain the measurement information measured by the body composition meter 10 and another measurement device, determine the level of health awareness of the user from the obtained measurement information in this communication terminal, and display the information on health according to the determination results in this screen.

The information processing device according to the present invention is not limited to be achieved as the functions of the body composition meter 10. For example, this information processing device may be achieved by a server communicable directly or indirectly with the body composition meter 10 or a function of another device such as the smart phone.

It should be noted that the display unit 3 described as the notifying means is one example. As long as means can transmit the information on health to the user, the means may use, for example, a sound or vibrations and therefore is not specifically limited.

This application claims priority based on Japanese Patent Application No. 2017-067426, filed with the Japan Patent Office on Mar. 30, 2017, the entire contents of which are incorporated into this specification by reference.

REFERENCE SIGNS LIST 1, 2 electrode
3 display unit (notifying means)
4 operating unit
5 load sensor
6 timer
7 biological impedance measuring unit
8 storage unit
10 body composition meter (information processing device)
15 degree-of-laziness index calculator (degree-of-laziness index calculating means)
17 variation cause determining unit (variation cause determining means)
20 control unit (obtaining means, determining means, and control means)
21 bioelectrical impedance calculator
22 health awareness level determining unit (determining means)
S1, S30, S31 (obtaining step)
S3, S33 to 35 (determining step)
S5 (notifying step)

What is claimed is:
1. An information processing device comprising:
a controller; and
a notifying unit configured to notify the user of information on health,
wherein the controller is programmed to:
obtain measurement information on a measurement habit when a user measures body information of himself/herself;
calculate a degree-of-laziness index as an index to measure the level of awareness on the basis of a trend specified from the measurement information;
determine a level of awareness of the user for health of himself/herself on the basis of the degree-of-laziness index; and
control the notifying unit so as to notify the user of information on health according to the level of awareness.

2. The information processing device according to claim 1, wherein
the measurement information includes a pattern index indicative of at least any one of measurement frequency and regularity when the user measures the body information of himself/herself.

3. The information processing device according to claim 1, wherein
the measurement information includes a variation index indicative of an amount of variation of the body information calculated on the basis of a plurality of measured values through measurements of the body information of himself/herself by the user in time series.

4. The information processing device according to claim 1, wherein
the body information is at least any one of a weight and a biological impedance of the user.

5. The information processing device according to claim 1, wherein
the measurement information includes a stepping way index indicative of a change in a load when the user measures the weight of himself/herself.

6. The information processing device according to claim 1, wherein
the controller is programmed to weight the measurement information obtained according to a level of contribution to the level of awareness.

7. The information processing device according to claim 1, wherein
the controller is further programmed to change at least one of an information volume and a level of a specialization regarding health to be notified by the notifying unit according to the level of awareness determined.

8. The information processing device according to claim 1, wherein
the controller is further programmed to:
determine a variation cause of the measurement information, and
control the notifying unit so as to notify the user of the information on health according to the variation cause determined.

9. A non-transitory computer-readable recording medium including a program that causes a computer configured to process measurement information on a measurement habit when a user measures body information of himself/herself to execute:
a calculating step of calculating a degree-of-laziness index as an index to measure the level of awareness on the basis of a trend specified from the measurement information,
a determining step of determining a level of awareness of the user for health of himself/herself on the basis of the degree-of-laziness index; and
a notifying step of notifying the user of information on health according to the level of awareness.

10. An information processing method comprising:
obtaining measurement information on a measurement habit when a user measures body information of himself/herself;
calculating a degree-of-laziness index as an index to measure the level of awareness on the basis of a trend specified from the measurement information,
determining a level of awareness of the user for health of himself/herself on the basis of the degree-of-laziness index; and
notifying the user of information on health according to the level of awareness.

\* \* \* \* \*